United States Patent
Thurner et al.

(10) Patent No.: US 10,391,203 B2
(45) Date of Patent: Aug. 27, 2019

(54) BODY MADE OF BONE SUBSTITUTE MATERIAL AND METHOD FOR PRODUCTION

(75) Inventors: Marc Thurner, Hauterive (CH); Michael Kuster, Bern (CH)

(73) Assignee: regenHU AG, Villaz-St-Pierre (CH)

( * ) Notice: Subject to any disclaimer, the term of this patent is extended or adjusted under 35 U.S.C. 154(b) by 1056 days.

(21) Appl. No.: 14/238,169

(22) PCT Filed: Aug. 8, 2012

(86) PCT No.: PCT/EP2012/065514
§ 371 (c)(1),
(2), (4) Date: Mar. 19, 2014

(87) PCT Pub. No.: WO2013/021000
PCT Pub. Date: Feb. 14, 2013

(65) Prior Publication Data
US 2014/0193776 A1   Jul. 10, 2014

(30) Foreign Application Priority Data
Aug. 11, 2011 (CH) ..................... 1330/11

(51) Int. Cl.
*A61C 8/00* (2006.01)
*A61L 27/56* (2006.01)
*A61L 31/14* (2006.01)
*A61F 2/28* (2006.01)
*A61B 17/86* (2006.01)

(52) U.S. Cl.
CPC ............ *A61L 27/56* (2013.01); *A61B 17/866* (2013.01); *A61B 17/8625* (2013.01); *A61C 8/0012* (2013.01); *A61C 8/0013* (2013.01); *A61F 2/28* (2013.01); *A61L 31/146* (2013.01); *A61B 17/8685* (2013.01); *A61B 17/8695* (2013.01); *A61B 2017/8655* (2013.01); *A61F 2002/2835* (2013.01); *A61F 2310/00179* (2013.01); *A61L 2430/02* (2013.01)

(58) Field of Classification Search
CPC ... A61C 8/0012; A61C 8/0013; A61C 8/0015; A61C 8/00–0098; A61L 27/56–58; A61B 17/8625; A61B 17/866
See application file for complete search history.

(56) References Cited

U.S. PATENT DOCUMENTS 3,465,441 A * 9/1969 Linkow ................ A61C 8/0019
433/176
4,599,085 A * 7/1986 Riess ...................... A61B 17/58
424/422
4,812,120 A * 3/1989 Flanagan ............. A61C 8/0012
433/173
(Continued)

FOREIGN PATENT DOCUMENTS

EP        1234552 A1   8/2002
EP      1 277 450 A2   1/2003
(Continued)

*Primary Examiner* — Yogesh P Patel
(74) *Attorney, Agent, or Firm* — Knobbe, Martens, Olson & Bear, LLP

(57) ABSTRACT

The invention relates to a biocompatible body to be implanted into a cavity of a bone, comprising a main structure made of a bone substitute material. According to the invention, the body has a connecting element, said connecting element being embedded at least partially in the main structure of the body.

16 Claims, 4 Drawing Sheets

(56) References Cited

U.S. PATENT DOCUMENTS

| | | | | |
|---|---|---|---|---|
| 5,062,798 A | * | 11/1991 | Tsuge | A61C 8/0012 433/173 |
| 5,344,457 A | * | 9/1994 | Pilliar | A61C 8/0012 433/174 |
| 2004/0053198 A1 | * | 3/2004 | Minevski | A61C 8/0012 433/201.1 |
| 2004/0064193 A1 | * | 4/2004 | Evans | A61L 27/12 623/23.51 |
| 2007/0015110 A1 | | 1/2007 | Zhang et al. | |
| 2007/0141106 A1 | * | 6/2007 | Bonutti | A61B 17/0401 424/423 |
| 2008/0241793 A1 | * | 10/2008 | Collins | A61C 8/0006 433/174 |
| 2009/0215007 A1 | * | 8/2009 | Caterini | A61L 27/047 433/173 |
| 2010/0003639 A1 | * | 1/2010 | Salvi | A61C 8/0012 433/174 |
| 2010/0003640 A1 | * | 1/2010 | Damstra | A61C 8/0012 433/201.1 |
| 2010/0206224 A1 | | 8/2010 | Thurner et al. | |
| 2011/0307073 A1 | * | 12/2011 | Teoh | A61F 2/28 623/23.61 |
| 2012/0214128 A1 | * | 8/2012 | Collins | A61C 8/0012 433/173 |

FOREIGN PATENT DOCUMENTS

| | | |
|---|---|---|
| JP | 03-292947 A2 | 12/1991 |
| JP | 2003-102755 A2 | 4/2003 |
| JP | 2005-065803 A2 | 3/2005 |
| JP | 2008-541874 A | 11/2008 |
| JP | 2010-131130 A | 6/2010 |
| WO | WO 2006/127392 A2 | 11/2006 |
| WO | WO 2007/027794 A1 | 3/2007 |
| WO | WO 2011/030185 A1 | 3/2011 |
| WO | WO 2011/075800 A1 | 6/2011 |

* cited by examiner

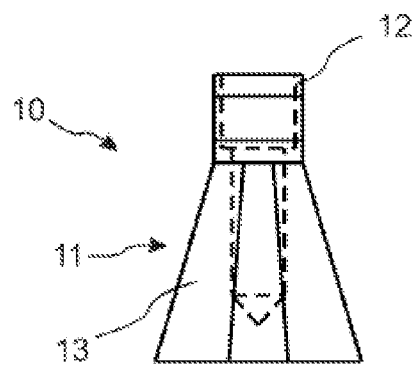
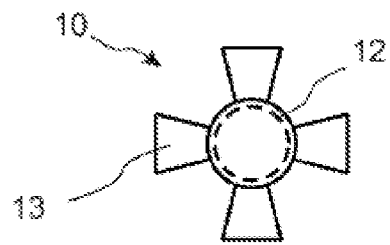
Fig.5(a)　　　　　　　　　　　　　　Fig.5(b)
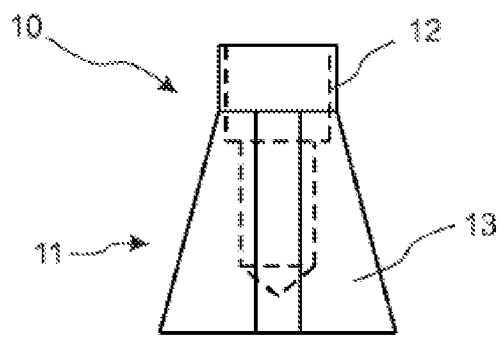
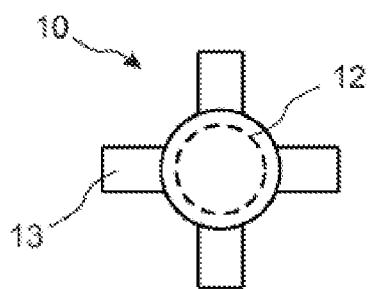
Fig.6(a)　　　　　　　　　　　　　　Fig.6(b)
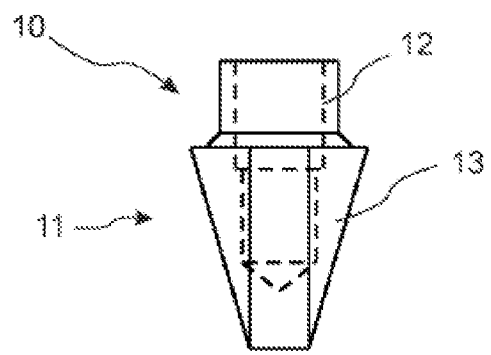
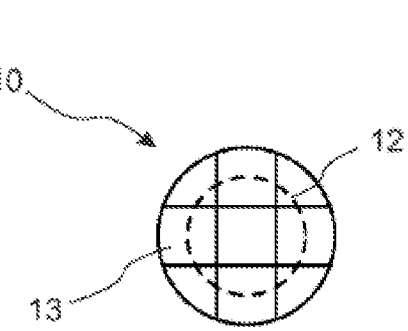
Fig.7(a)　　　　　　　　　　　　　　Fig.7(b)

BODY MADE OF BONE SUBSTITUTE MATERIAL AND METHOD FOR PRODUCTION

This application is the U.S. National Phase under 35 U.S.C. § 371 of International Application No. PCT/EP2012/065514, filed Aug. 8, 2012, which claims priority to Swiss Application No. 01330/11, filed Aug. 11, 2011.

TECHNICAL FIELD

The invention pertains to a biocompatible body for implanting into a cavity of a tissue, such as bone, comprising a main structure made from a bone substitute material. Moreover, the invention pertains to a method for the production of a biocompatible body for implanting into a cavity of a tissue, such as bone.

PRIOR ART

Synthetic or natural bone substitute material is used in medicine, especially in dentistry for tooth implantation, in order to fill in defects or cavities in the bone. The materials are porous and often fortified with substances, which promote bone formation (osteoinductive substances). Oftentimes in those suffering from osteoporosis of the jaw due to tooth loss or periodontitis there is not enough bone present, so that time-consuming bone construction procedures are required before undertaking a tooth implant. Therefore, several surgical operations are often needed for the treatment. In a first surgical operation, a bone substitute material is introduced into a cavity in the jawbone or in the regions where not enough bone is present due to osteoporosis. To enable an undisturbed regeneration, the introduced bone substitute material must often be protected in a complicated and difficult operation with a membrane (such as a Bio-Gide® membrane from Geistlich AG). The membrane, among other things, prevents soft tissue from growing into the cavity filled with bone substitute material. After this, the introduced bone substitute material is gradually interpenetrated with or replaced by newly formed bone during a regeneration time of several months (osteoconduction). After the regeneration period, in a second surgical operation, an implant body is inserted into the newly formed bone, on which in a later step an abutment is put in place afterwards, or directly a crown, a bridge, or some other denture. Surgical operations are costly and there is always a risk of infection. Furthermore, the inserting of an implant leads to post-operative pain at the implantation site. The quality of life of the patient is also greatly impaired during the regeneration period. For example, the regeneration times between the two surgical operations for a single tooth implantation typically take three to six months.

PRESENTATION OF THE INVENTION

The problem of the invention is to provide a biocompatible body of the kind mentioned above for simplified implantation into a cavity of a bone, which reduces the treatment costs and the risk of infection of a patient during a tooth implantation, for example. Furthermore, the quality of life of the patient should be improved during the entire procedure.

This problem is solved by the features of claim 1. The biocompatible body of the aforementioned kind according to the invention is characterized in that the body has a connection element, and the connection element is at least partly embedded in the main structure of the body.

In a simple surgical operation, the body according to the invention can be inserted into a cavity in the bone, wherein the main structure of the body fills up the cavity or the regions where there is insufficient bone due to osteoporosis. After this, the main structure of bone substitute material of the introduced body is gradually interpenetrated or replaced by newly formed bone during a regeneration time of several months. After the regeneration time, an abutment can be placed on the connection element, or directly a crown, a bridge, or some other denture. A complicated and difficult operation to install a membrane and/or a further surgical operation to insert an implantation body in the newly formed bone is no longer necessary. The biocompatible body according to the invention thus makes it possible to perform, in a single surgical operation, treatments which often required two surgical operations and thus lead to a higher risk of infection, higher treatment costs, post-operative pain at the implant site, and a worse quality of life due to the long period between the two operations. In this way, the costs and the risk of infection can be lowered, and the long waiting time between the operations can be avoided.

In a first preferred embodiment of the biocompatible body according to the invention, the connection piece has a head, which is embedded in the main structure of the body such that the main structure encloses the head of the connection piece like a collar. The connection piece can be, e.g., a traditional tooth implant, a screw, or a connection piece specially fabricated for the embedding. The connection piece can also have an anchoring segment, with which it can be installed in the existing bone, while the main structure of the body fills up the cavity in the bone or the regions where insufficient bone is present due to osteoporosis.

In a second preferred embodiment of the biocompatible body according to the invention, the connection piece has an anchoring segment, while the connection element with the anchoring segment is embedded by the anchoring segment in form-fitting manner in the main structure of the body. The connection piece can be a traditional tooth implant or a connection piece specially fabricated for the embedding. In this embodiment, the biocompatible body can be inserted into a cavity of the bone.

Since the connection piece is embedded in the main structure made of bone substitute material, or enclosed with form fitting by the bone substitute material, a greater diversity is possible for the anchoring segment. It is not necessary for the anchoring segment to have a shape by which it can be driven or screwed into a main structure. Neither does the connection piece have to be glued nor cemented firmly in the main structure.

Bone substitute material means a material, which is used for the filling up of bone defects or major cavities in the bone, during a tooth implantation, for example. It should prevent an interpenetration of the cavity with soft tissue and promote the buildup of bone. The newly formed bone can grow together with the bone substitute material or the bone substitute material can be partly or entirely broken down and replaced by the newly formed bone. The bone substitute material can be synthetic or natural.

The main structure of the body is preferably made from a shape-stable but easily worked bone substitute material, so that the shape of the body prior to being inserted into the cavity of the bone or the regions where insufficient bone is present due to osteoporosis can be adapted to the shape of the cavity or the region. The main structure can also be molded directly so that it is fitted into the cavity or the region.

In all embodiments, the connection element preferably has a receiving opening for a connection or terminating element. The receiving opening can be accessible from outside the main structure of the body for the connection or terminating element. It can also lie in the main structure of the body and be opened up only prior to inserting the body into the cavity of the bone. Furthermore, it can be closed with a closure element, such as a cover, which can be removed before putting the connection or terminating element in place.

In another preferred embodiment, the anchoring segment is shaped so that it is embedded in the main structure secure against twisting. This can be accomplished, e.g., by a noncircular cross section of the anchoring segment. Such a twist-proof shape of the anchoring segment has, e.g., a rectangular cross section, or ribs, wings, fins, knobs, hooks, projections, plates, lattices or the like are formed on it.

In addition to or independently of the twist-proof shape, the anchoring segment of the body according to the invention preferably has an undercut, by which it engages with the main structure, so that the anchoring segment cannot be pulled out from the main structure without damaging it. This can be accomplished, e.g., by different size cross sections of the anchoring element or by recesses in the connection element with which the main structure can engage.

In all embodiments, the connection element can be fashioned as a single piece or a multiple piece. The connection element is preferably made of ceramics, metal, polymer or plastic. Furthermore, the main structure can be osteoconductive, to improve the bone formation. This can be accomplished, e.g., by voids or pores, which can be additionally fortified with osteoinductive compounds and/or pharmaceutical products. Other bioactive substances with different functions can also be placed in the voids, such as substances that prevent soft tissue from growing into the main structure.

One speaks of a substance being osteoinductive (osseoinductive) when it is capable of stimulating bone formation. When a material is able to facilitate natural bone growth as a scaffolding, one speaks of osteoconduction. Such a material is osteoconductive or it has an osteoconductive structure.

Preferably, the main structure has a macroporous, interconnected structure. For example, the main structure can be a gyroid or gyroid-like structure.

Moreover, the main structure can have a closed structure on the sides which are facing soft tissue in the implanted state, in order to prevent an ingrowing of soft tissue and a concomitant reduction of the bone restructuring in dental applications, for example. A membrane as recommended in other traditional dental applications is therefore not necessary.

Preferably, the bone substitute material comprises, as a structurizing composition, a material chosen from the group of calcium phosphate, preferably calcium hydroxyapatite ($Ca_{10}(PO_4)_6(OH)_2$, HA), beta-tricalcium phosphate ($Ca_3(PO_4)_2$, beta-TCP) or biphasic calcium phosphate; bioglass; biopolymer, preferably polylactic acid or polylactide (PLA), poly-L-lactide (PLLA), chitosan, collagen, alginates, silicone, synthetic hydrogels or hyaluronane; and mixtures thereof.

As the osteoinductive compounds, one can use, e.g., bone marrow extract, pallet-rich plasma (PRP), thrombocyte mediator concentrate (TMC) or synthetic factors such as rhBMP (recombinant human bone morphogenetic proteins).

In another embodiment, the biocompatible body has, in addition to the main structure of bone substitute material, a second main structure of a biocompatible material, preferably a cartilage substitute material or soft tissue substitute, such as a skin tissue substitute. The biocompatible material can be a material based on collagen. The second main structure can be arranged on or in the main structure of bone substitute material and is constructed by the same method, by with different materials.

The invention moreover pertains to a method for the production of a biocompatible body according to the invention for implanting into a cavity of a bone. The method comprises the following steps: (i) preparation of a connection element; and (ii) emplacement of a main structure of bone substitute material, so that the connection element is embedded in the main structure of bone substitute material.

Preferably, for the production of the biocompatible body according to the invention for implantation in a cavity of a bone, one uses a method for the production of blocks of bone substitute material, as is described in WO 2009/040352. In the method, a main structure of bone substitute material is built up in several layers, one on top of another. The layers each time comprise several lines of bone substitute material, spaced apart from each other and preferably running in parallel with each other. In addition, an osteoinductive compound can be introduced into the interstices between the lines of a layer. With the method, one can produce a bone substitute material in three-dimensional blocks with the desired shape, or a composite consisting of several materials. These have a macroporous, interconnected structure. In this regard, reference is made to the application WO 2009/040352, whose content is hereby taken up into this application. The method can also be used to produce bodies with any desired external and internal structure, the material being deposited layer by layer in the form of single points or short lines. For example, the method makes it possible to produce a gyroid or gyroid-like structure.

In the preferred production method, a main structure of bone substitute material is built up layer by layer around the connection element, until the latter is at least partly embedded in the main structure. Twist-proof elements and undercuts of the anchoring segment can also be completely embedded or enclosed by the main structure. The lines of the layer being deposited preferably make an angle, preferably an angle of 30 to 90 degrees, with the lines of the previous layer, so that a macroporous, interconnected structure is formed, which can be filled up with osteoinductive compounds and/or pharmaceutical or bioactive products. A body having such a macroporous, interconnected structure can be secured to a bone, e.g., by suturing. However, the layers need not be deposited as continuous lines at a particular angle to each other. The layers can be deposited in any given manner one after another, so that one can also make structures such as the aforementioned gyroid or gyroid-like structures.

In another embodiment of the method according to the invention, the main structure of bone substitute material can be cast or foamed around the anchoring segment.

The biocompatible body with the connection element can be used preferably in dentistry for tooth implantation. A use as a connection for an artificial joint, such as a finger joint, is likewise possible.

BRIEF EXPLANATION OF THE DRAWINGS

The invention shall now be explained more closely by means of sample embodiments in connection with the drawing. There are shown:

FIG. 5, an embodiment of a connection element: (a) in a side view and (b) in a bottom view;

FIG. 6, another embodiment of a connection element: (a) in a side view and (b) in a bottom view;

FIG. 7, another embodiment of a connection element: (a) in a side view and (b) in a bottom view;

WAYS OF IMPLEMENTING THE INVENTION

Figure 1A:
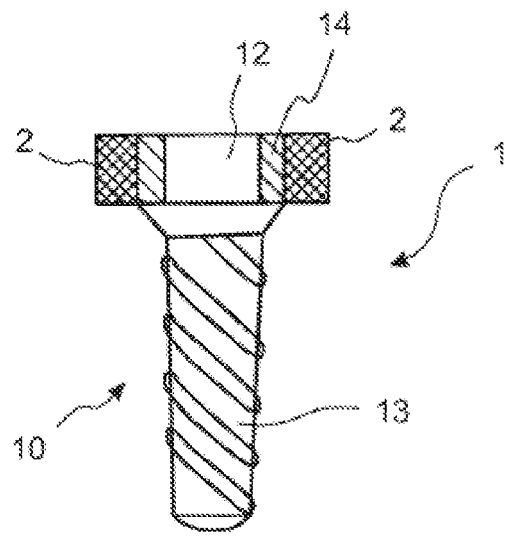
FIG. 1, an embodiment of a body according to the invention with embedded connection element, (a) in a side view with a cross section through the head along line C-C of FIG. 1 (b), and (b) in a top view.
Figure 1B:
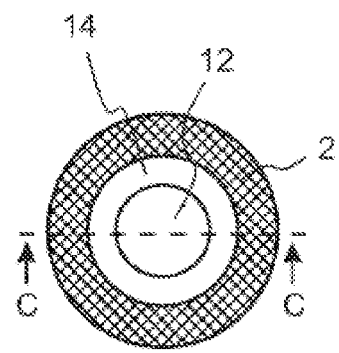

FIG. 1 shows an embodiment of a body 1 according to the invention with embedded connection element 10. In (a), the body is shown in a side view with section through a head 14 of the connection element 10 along line C-C per FIG. 1 (b). In (b), the body 1 is shown in a top view of a receiving opening 12 of the connection element 10. The connection element is, e.g., a traditional dental implant, which has an anchoring segment fashioned as a "screw". The body 1 comprises moreover a main structure 2 of a biocompatible bone substitute material, in which the head 14 of the connection element 10 is embedded, so that the main structure 2 encloses the head 14 as a collar. The main structure 2 is shown as a cylindrical body, but it can also have other shapes depending on the shape of the cavity in which the body is being inserted. Furthermore, the main structure can be made from a shape-stable but easily worked material, so that it can be easily adapted to the shape of the cavity before being inserted. Other attributes of the main structure are described further below.

Figure 9:
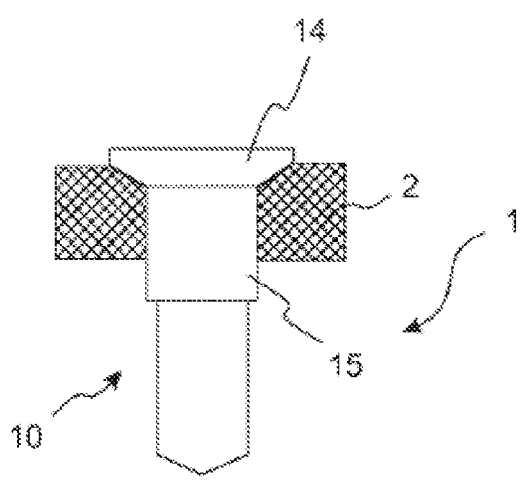
FIG. 9, another embodiment of a body according to the invention with embedded connection element.

FIG. 9 shows another embodiment of a body 1 according to the invention with embedded connection element 10. In contrast to the embodiment in FIG. 1 (a), the connection element is a screw, e.g., a countersunk screw, and it is embedded partly in the main structure 2 by a head region 14 and/or neck region 15 of the screw.

Figure 2:
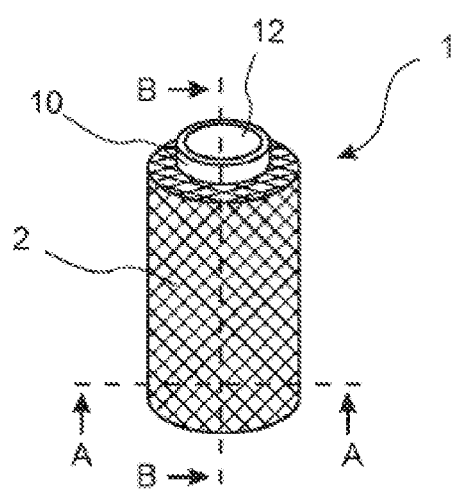
FIG. 2, a perspective view of an embodiment of the body according to the invention with embedded connection element.

FIG. 2 shows a perspective view of an embodiment of a body 1 according to the invention with embedded connection element 10. The body 1 comprises a main structure 2 of a biocompatible bone substitute material. In contrast with the embodiment of FIG. 1, a connection element 10 with an anchoring segment 11 (not evident in FIG. 2) is embedded in the main structure. Only the receiving opening 12 of the connection element can be seen in FIG. 2, projecting slightly beyond the main structure 2 of the body 1. The main structure 2 is shown as a cylindrical body, but it can also have other shapes depending on the shape of the cavity in which the body is to be inserted. Furthermore, the main structure can be made from a shape-stable but easily worked material, so that it can be easily adapted to the shape of the cavity before being inserted.

Figure 3:
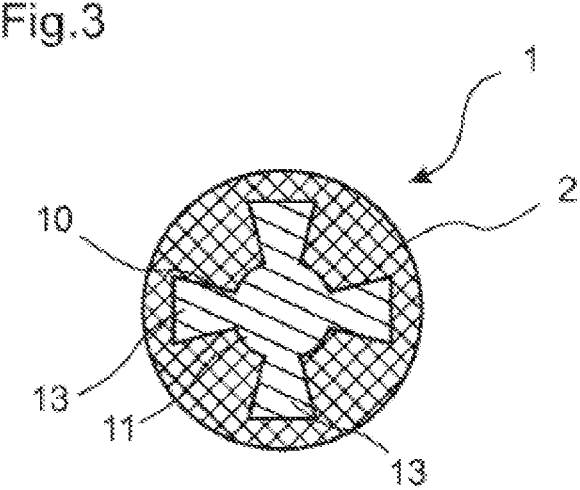
FIG. 3, a cross section along line A-A per FIG. 2 of an embodiment of a body according to the invention with embedded connection element.

FIG. 3 shows a section along line A-A, as represented in FIG. 2, of an embodiment of a body 1 according to the invention with embedded connection element 10. The broken line shows the receiving opening 12. The connection element 10 has wings 13 directed radially outward in the anchoring segment 11, broadening toward the outside. In this way, the connection element 10 is embedded in the main structure 2 of the body 1 and prevented from twisting.

Figure 4:
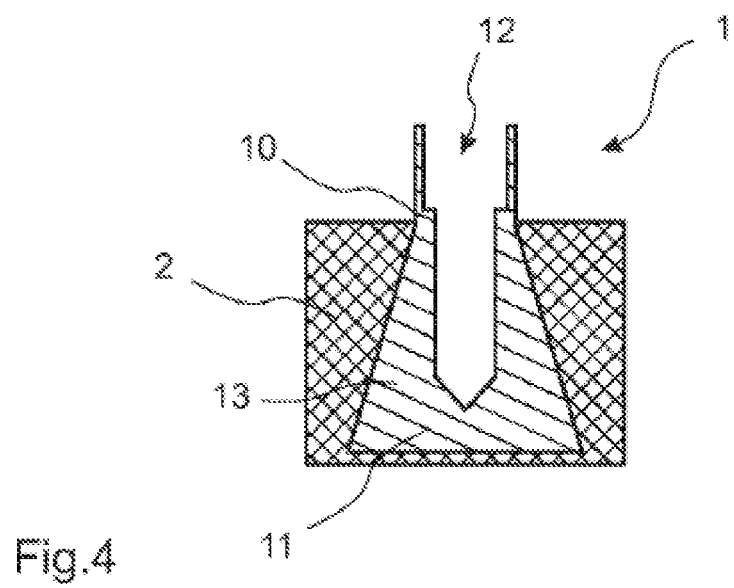
FIG. 4, a cross section along line B-B per FIG. 2 of an embodiment of a body according to the invention with embedded connection element.

FIG. 4 shows a section along line B-B, as represented in FIG. 2, of an embodiment of the body 1 according to the invention per FIG. 3 with embedded connection element 10. The outwardly directed wings 13 broaden from the receiving opening in the downward direction. From below, i.e., in the direction of the receiving opening, the anchoring segment 11 of the connection element 10 has an undercut, which engages with the main structure 2 of the body 1, so that the connection element 10 cannot be pulled out from the main structure 2 without damaging it.

The main structure 2 has voids or pores, as represented by the cross hatching in FIGS. 1 to 4. Preferably, the main structure has a macroporous, interconnected structure. The main structure can have, e.g., a gyroid or gyroid-like structure. These voids can be filled or fortified with osteoinductive compounds and/or pharmaceutical or bioactive products.

FIGS. 5 to 7 show three different embodiment of a connection element 10: (a), in a side view, and (b), in a bottom view. The broken line each time shows a receiving opening 12 for connection or termination elements. The three connection elements differ from each other each time in the configuration of the anchoring segments 11. The configuration in FIG. 5 has an anchoring segment with four side wings 13, which broaden radially outward. By contrast, the winds of the configuration in FIGS. 6 and 6 are of equal width toward the outside. In all three embodiments, the wings 13 provide a twist-proof anchoring in a main structure 2 of a body 1 according to the invention. A connection element so embedded in the main structure 2 cannot be twisted from the main structure 2 without damaging it.

Furthermore, the embodiments shown in FIGS. 5 to 7 have an undercut in the anchoring segment 11, looking from below in the direction of the receiving opening 12, so that a connection element embedded in the main structure 2 engages by the undercut with the main structure 2. In the embodiments in FIGS. 5 and 5 this is accomplished in that the width of the wings 13 increases from the receiving opening toward the bottom. In the embodiment of FIG. 7, the wings are just the opposite, so that the width of the wings 13 decreases from the receiving opening 12 toward the bottom, and these are completely embedded in the main structure. Connection elements embedded in this way cannot be pulled out from the main structure 2 without damaging it.

Other shapes of the anchoring, especially a twistproof anchoring, are also possible. For example, the anchoring segment can have an angled cross section, especially a rectangle. Instead of the wings, elements such as ribs, fins, knobs, hooks, projections, shaped plates, lattices or the like can also be formed. Moreover, the number of these elements can vary.

The aforementioned undercut can also be accomplished by cross sections of different size for the anchoring element or by recesses in the connection element with which the main structure can engage.

Figure 8:
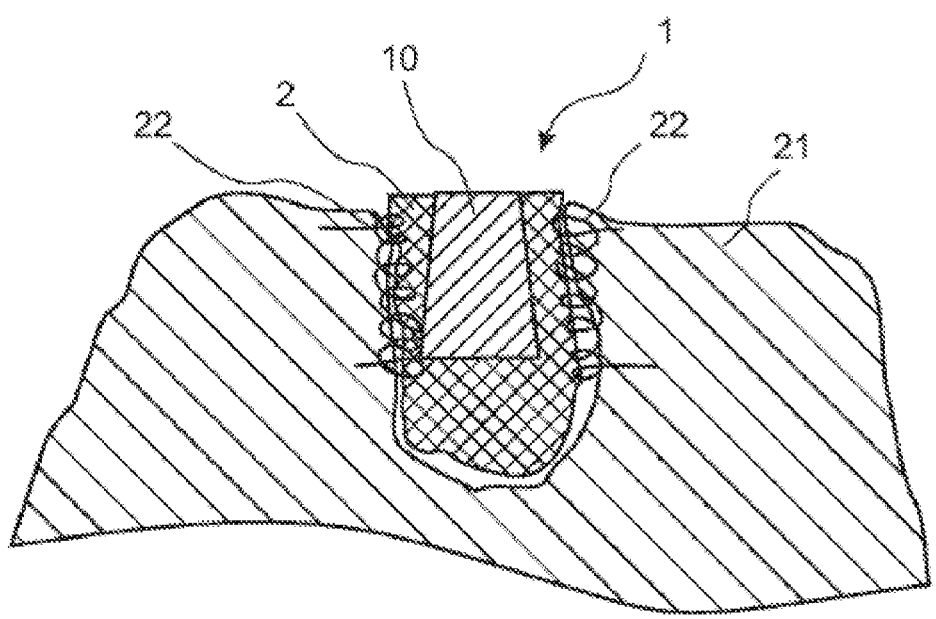
FIG. 8, a schematic representation of a sutured body according to the invention.

FIG. 8 shows a schematic representation of a body 1 according to the invention with embedded connection element 10. As in the other embodiments of FIGS. 1 to 4, the main structure 2 of the body 1 has a macroporous, interconnected structure. This structure can be used to suture the body 1 to the bone 22 by means of one or more threads 22.

LIST OF REFERENCES

1 body
2 main structure
10 connection element
11 anchoring segment
12 receiving opening
13 wing
14 head
15 neck
21 bone
22 thread

What is claimed is:

1. A biocompatible body for implanting into a cavity of a bone, comprising:
   a main structure made from a bone substitute material, wherein the main structure comprises a plurality of layers on top of each other and wherein each of the layers comprises a plurality of lines made of bone substitute material, each of the lines of each layer being spaced apart from each other, wherein the body comprises a connection element, the connection element comprising an anchoring segment, the anchoring segment embedded in the main structure of the body, wherein the connection element comprises a receiving opening for a joining or sealing element and the receiving opening is accessible for the joining or the sealing element from outside the main structure, and wherein the anchoring segment comprises outwardly directed wings that widen downward from the receiving opening.

2. The biocompatible body according to claim 1, wherein the connection element has a head, which is embedded in the main structure of the body such that the main structure encircles at least a portion of the head of the connection element.

3. The biocompatible body according to claim 1, wherein the connection element has an anchoring segment, while the connection element is embedded by the anchoring segment in the main structure of the body.

4. The biocompatible body according to claim 3, wherein the anchoring segment is shaped to secure against twisting.

5. The biocompatible body according to claim 3, wherein the anchoring segment of the connection element has an undercut, by which the connection element engages with the main structure.

6. The biocompatible body according to claim 3, wherein the connection element is enclosed with form-fitting by the main structure of the body.

7. The biocompatible body according to claim 1, wherein the receiving opening is configured for a connection element or terminating element.

8. The biocompatible body according to claim 1, wherein the receiving opening is accessible from outside the main structure of the body for the connection element or terminating element.

9. The biocompatible body according to claim 1, wherein the connection element is fashioned as a single piece.

10. The biocompatible body according to claim 1, wherein the connection element is made of ceramics, metal, polymer or plastic.

11. The biocompatible body according to claim 1, wherein the main structure of bone substitute material is osteoconductive.

12. The biocompatible body according to claim 1, wherein the main structure of bone substitute material has voids fortified with an osteoinductive compound and/or pharmaceutical or bioactive products.

13. The biocompatible body according to claim 1, wherein the main structure has a macroporous, interconnected structure, having a gyroid or gyroid-like structure.

14. The biocompatible body according to claim 1, wherein the shape of the main structure is adapted to the shape of the cavity in the bone.

15. The biocompatible body according to claim 1, wherein the biocompatible body has a second main structure of a biocompatible material.

16. The biocompatible body according to claim 15, wherein the biocompatible material is a cartilage substitute material or soft tissue substitute.

* * * * *